(12) United States Patent
Colle et al.

(10) Patent No.: US 9,371,267 B2
(45) Date of Patent: Jun. 21, 2016

(54) CERIUM CATALYZED PRODUCTION OF SECONDARY ALCOHOLS AND PLASTICIZERS BASED ON THE SECONDARY ALCOHOLS

(75) Inventors: Karla S. Colle, Magnolia, TX (US); Allen D. Godwin, Seabrook, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 665 days.

(21) Appl. No.: 13/513,156

(22) PCT Filed: Nov. 16, 2010

(86) PCT No.: PCT/US2010/056842
§ 371 (c)(1),
(2), (4) Date: Aug. 3, 2012

(87) PCT Pub. No.: WO2011/075259
PCT Pub. Date: Jun. 23, 2011

(65) Prior Publication Data
US 2012/0289636 A1    Nov. 15, 2012

Related U.S. Application Data

(60) Provisional application No. 61/287,636, filed on Dec. 17, 2009.

(30) Foreign Application Priority Data

Feb. 12, 2010  (EP) .................................... 10153504

(51) Int. Cl.
  *C07C 29/09*   (2006.01)
  *C07C 67/04*   (2006.01)
  *C07C 67/08*   (2006.01)

(52) U.S. Cl.
  CPC ............. *C07C 67/04* (2013.01); *C07C 29/095* (2013.01); *C07C 67/08* (2013.01)

(58) Field of Classification Search
  CPC ...... C07C 67/04; C07C 29/095; C07C 31/02; C07C 31/125
  See application file for complete search history.

(56) References Cited

U.S. PATENT DOCUMENTS

| 3,542,857 A * | 11/1970 | Lutz ............................. 560/246 |
| 4,365,084 A | 12/1982 | Young |
| 4,461,729 A * | 7/1984 | Young ............................. 558/41 |
| 2004/0102643 A1* | 5/2004 | Tway ............................. 558/325 |

FOREIGN PATENT DOCUMENTS

| GB | 1 012 821 | 12/1965 |
| WO | WO 2009/070398 | 6/2009 |
| WO | WO 2009/070399 | 6/2009 |

OTHER PUBLICATIONS

Horiuchi et al. J. Chem. Research (S), 2003, 5, 270-272.*
Horiuchi et al., "Esterification of alkene with cerium (IV) sulfate in carboxylic acid," Journal of Chemical Research, Synopses, (5), 2003, pp. 270-272, CODEN: JRPSDC; ISSN: 0308-2342, 2003.
Kaulen, "Inversion der Alkohol-Konfiguration über in situ dargestellte Isoharnstoff-ether," Angewandte Chemie, vol. 99, No. 8, 1987, pp. 800-802 (XP002589586).

* cited by examiner

*Primary Examiner* — Michael Pepitone
(74) *Attorney, Agent, or Firm* — Leandro Arechederra, III

(57) ABSTRACT

A method for preparation of secondary alcohols with a high proportion of hydroxyl group at the C2 position is disclosed. Alkyl carboxylates, high in alpha-methylcarboxylate content, are produced via reaction of an alpha-olefin and a carboxylic acid in the presence of a cerium catalyst. The resultant alkyl carboxylate is hydrolyzed to yield a secondary alcohol with a high 2-hydroxyl content. The secondary alcohol may be used to prepare esters, especially phthalate esters or cyclohexanoate diesters, which are useful as plasticizers. These esters are more effective as plasticizers than esters derived from other secondary alcohols due to their high C2 point of attachment.

6 Claims, No Drawings

CERIUM CATALYZED PRODUCTION OF SECONDARY ALCOHOLS AND PLASTICIZERS BASED ON THE SECONDARY ALCOHOLS

CROSS REFERENCE TO RELATED APPLICATIONS

This application is a National Stage entry under 36 U.S.C. §371 of International Application No. PCT/US2010/056842, filed Nov. 16, 2010, which claims the benefit of Ser. No. 61/287,636, filed Dec. 17, 2009, herein incorporated by reference in their entireties.

FIELD OF THE INVENTION

The invention relates to a method of making secondary alcohols using cerium catalysts, said alcohols characterized as having a high 2-hydroxyl content, and also to compositions made from said alcohols.

BACKGROUND OF THE INVENTION

Phthalates and many other esters are well-known as plasticizers for PVC. These esters are commonly produced by esterification of an acid (or anhydride) with a primary alcohol. Esters may also be derived from secondary alcohols.

The effectiveness of secondary alcohol esters as plasticizers is known to be dependent on the position of the hydroxyl group in the alcohol molecule. Secondary alcohol esters with a high degree of hydroxyl content at the second carbon are considerably more effective than if the hydroxyl group is located more toward the interior of the carbon chain. The use of secondary alcohol esters as plasticizers has been limited by the availability of secondary alcohols with a high C2 hydroxyl content (high C2-OH). 2-Octanol or capryl alcohol obtained from castor oil, is available in limited quantities. For many years dicapryl phthalate was available as a plasticizer for flexible PVC, however because of the costs of the alcohol, this product is not longer available in commercial quantities. Higher molecular weight secondary alcohols are also of interest in surfactant applications where they have improved properties such as wetting efficiency over surfactants derived from primary alcohols. Secondary higher alcohol alkoxylates are advantaged over comparable primary alcohol alkoxylates by having lower pour points, less foam, and excellent detergency and emulsifying power.

The use of esters of secondary alcohols as plasticizers in various polymeric systems has recently been described in WO 2009-070398 and WO 2009-070399.

Most secondary alcohols are commercially produced today by oxidation of paraffins. This process is not suitable for production of secondary alcohols for plasticizer use since it is non-selective and produces a broad mixture of products with the OH group located all along the hydrocarbon backbone. Selective direct hydration of C5 to C12 olefins to C5 to C12 secondary alcohols is not a viable process for it produces secondary alcohols with minimal C-2 substitution.

One route to secondary alcohols with a high degree of C2-OH is the reaction of an olefin with a carboxylic acid in the presence of certain zeolite catalysts. This reaction must be conducted at ~200° C./200 psig and gives conversions on the order of 25-30% in 5 hours. Another route to secondary alcohols with high C2-OH content is therefore desired.

There is one literature report of esterification of alkenes with Ce(IV) sulfate to produce carboxylic acid esters. While the selectivity is high, the activity of this catalyst system is too low to be commercially acceptable.

The present inventors have discovered that secondary alcohols, such as in the plasticizer range (C4-C13), with a high degree of alcohol substitution at the 2 position (C2-OH) can be prepared with commercially acceptable selectivity and activity by the reaction of an α-olefin with a carboxylic acid in the presence of certain cerium catalysts other than Ce(IV) sulfate. The resultant alkyl carboxylate, with a high α-methyl alkyl carboxylate content, can be hydrolyzed to yield the secondary alcohol with a high degree of 2-hydroxy isomer, with very little, if any 3-hydroxy or higher structural isomer by-product.

SUMMARY OF THE INVENTION

The invention is directed to a method for preparation of secondary alcohols with a high proportion of hydroxyl group at the C2 position by reaction of an alpha-olefin and a carboxylic acid in the presence of certain cerium catalysts. The resultant alkyl carboxylate is hydrolyzed to yield a secondary alcohol with a high 2-hydroxyl content. The C2-OH alcohol of interest may be represented in the conventional manner as R—C(H)(OH)—CH$_3$.

In embodiments, for use in preparing esters useful as plasticizers, R will generally be aliphatic and of a straight chain, although some branching may be permitted, and contain from 1 to 18 carbon atoms, such as 2 to 11 carbon atoms, or 5 to 12 carbon atoms, or 4 to 10 carbon atoms, or 7 to 9 carbon atoms, or other ranges such as from any of the lower numbers just mentioned to any of the higher numbers just mentioned.

The invention is also directed to the preparation of esters, such as phthalate or terephthalate or benzoate or trimellitate or cyclohexanoate esters, and mixtures thereof, of the high 2-hydroxl content secondary alcohols (C2-OH), and to compositions comprising such esters and plasticizable resins, particularly PVC.

In embodiments, the Ce(IV) catalysts effective for the process of the invention can be characterized as having a higher acidity than anhydrous Ce(IV) sulfate. In other embodiments the Ce(IV) catalysts can be characterized as Ce(IV) sulfates other than the anhydrous Ce(IV) sulfate, e.g., Ce(IV) with waters of hydration, or sulfates derivatized to be stronger acids, such as the per se well-known triflate moiety (OSO$_2$CF$_3$). In still other embodiments, the Ce(IV) catalyst may be characterized as Ce(IV) salts dispersed on supports.

It is an object of the invention to provide a selective process and high activity process for producing 2-hydroxyl content secondary alcohols of a carbon number range such as C5 to C12, the esters made therefrom, and plasticizable resin compositions made from such esters.

In embodiments, the process of the invention will provide a mixture of isomers, such as from 60-90 mol % C2-OH, or 70-80 mol %, or 60-80 mol %, or 70-90 mol %.

These and other objects, features, and advantages will become apparent as reference is made to the following detailed description, preferred embodiments, examples, and appended claims.

DETAILED DESCRIPTION

In an embodiment of the invention, secondary alcohols with a high proportion of hydroxyl group at the C2 position are prepared using certain cerium catalysts.

In another embodiment, alkyl carboxylates, high in alpha-methylcarboxylate content, are produced via reaction of an alpha-olefin and a carboxylic acid in the presence of a cerium catalyst. The resultant alkyl carboxylate is hydrolyzed to yield a secondary alcohol with a high 2-hydroxyl content. The secondary alcohol may be used to prepare esters, especially phthalate esters or adipate esters or trimellitate esters or citrate esters or terephthalate esters or benzoate esters or cyclohexanoate diesters, and mixtures thereof, which are useful as plasticizers. Without wishing to be bound by theory, these esters are more effective as PVC plasticizers than esters derived from other secondary alcohols due to their high C2 point of attachment.

Work by J. W. Hayden in Society of Plastics Engineering, Annual Technical Conference, 28th (1970), pp. 46-47, SPE Publisher, Greenwich Conn., reported that the performance of phthalate esters prepared with secondary alcohols, diminishes significantly as the C2-OH substitution is changed from the C2 position to C3, C4, and C5. Secondary alcohol phthalate esters made with C2-OH rich blends will have very good performance in PVC plasticizer efficiency, low temperature flexibility, lower volatility and lower plastisol viscosity while other secondary alcohol phthalate esters prepared with reduced on no C2-OH substituted alcohols, show decreased to unacceptable performance in these areas.

The cerium catalysts used in this study can be prepared by a variety of known processes. Many of these are prepared by the reaction of cerium dioxide or cerium tetrahydroxide with strong acids. For example $Ce(SO_4)_2$ can be prepared by heating $CeO_2$ with concentrated sulfuric acid, then isolating the $Ce(SO_4)_2$ as a yellow powder. $Ce(SO_4)_2.4H_2O$ can be prepared by dissolving $Ce(OH)_4$ in dilute sulfuric acid, heating, concentrating the salt by partial evaporation of the water, and isolating the product as bright orange crystals. Substitution of sulfuric acid with other acids will yield other cerium salts. One of skill in the art can prepare these catalysts without undue experimentation.

The first step in the process to prepare these high C2-OH content secondary alcohols is the reaction of an α-olefin with a carboxylic acid in the presence of particular cerium catalysts to selectively produce an alkyl carboxylate ester product enriched in the α-methylalkyl carboxylate ester. One of the advantages of the present invention is that the reaction may be carried out at very modest temperature (~90° C.) and atmospheric pressure. Conversions range from 40-70% in 2 hours with selectivity to the 2-isomer of, in embodiments, greater than 60%, such as from 60 to 90% or in other embodiments from 90 to nearly 100%, or in embodiments from 70 to 95%, 80-90%, 75-99%, and so forth, with other ranges contemplated such as from any of the lower ranges just mentioned to any of the higher ranges just mentioned. These percentages are of course mol %.

Suitable α-olefins for this process include but not limited to are hexene-1, heptene-1, octene-1, nonene-1, decene-1, undecene-1, dodecene-1, tridecene-1, and tetradecene-1, substituted α-olefins such as 3-methyl heptene-1, 4-methyl heptene-1, 5-methyl heptene-1, 6-methyl heptene-1, 3-methyl octene-1, 4-methyl octene-1, 5-methyl ocetene-1, 6 methyl octene-1, 7-methyl octene-1, 3 methyl nonene-1, 4 methyl nonene-1, 5 methyl nonene-1, 6 methyl nonene-1, 7 methyl nonene-1, 8 methyl nonene-1, similar methyl substituted olefins ranging in carbon number from C5 to C18 or linear olefin mixtures containing greater than 50% of the linear α-olefins.

Carboxylic acids used to make the carboxylate esters include formic acid, acetic acid or acetic anhydride, propanoic acid, butyric acid, isobutyric acid, pentanoic acid, isopentanoic acid, neopentanoic acid, hexanoic acid, isohexanoic acid, heptanoic acid, isoheptanoic acid, and 2-ethyl hexanoic acid.

These α-methylalkyl carboxylate esters can be prepared according to the following: to a 25 ml 3 necked flask equipped with magnetic stirrer and reflux condensor, is charged 10 ml of a mixture of glacial acetic acid and octene-1, in a 4:1 ratio. The catalyst is added at about the 0.1 to 2 gram level, and the reaction mixture heated with stirring, under reflux, for 2 hours. The secondary alkyl acetate esters are diluted with water, extracted into ether, neutralized by washing with dilute sodium bicarbonate solution and the solvent evaporated. The resulting products are analyzed by gas chromatography and by NMR spectroscopy. Results using various catalysts are shown in the following Table 1.

The α-methylalkyl carboxylate esters prepared according to this procedure can be produced with the ratio of acid to olefin varying from 1.5 to 6.0. In larger scale processes, both the acid and the catalyst can be recycled.

TABLE 1

| Catalyst | Catalyst Loading (Mole % Metal based on octene) | Reaction Time (hr) | Conversion of 1-Octene (mole %) | Selectivity to 2-Octyl Acetate |
|---|---|---|---|---|
| $Ce(SO_4)_2$ (anhyd) | 5.0 | 2 | 7.0 | 100 |
| $Ce(SO_4)_2 \cdot 4H_2O$ | 5.0 | 2 | 43.8 | 100 |
| $Ce(OSO_2CF_3)_4$ | 5.0 | 2 | 61.3 | 92.6 |
| Ce on $SiO_2$ | 2.8 | 2 | 68 | 100 |
| $Sc(OSO_2CF_3)_3$ | 5.0 | 5 | 95.3 | 58.6 |

The previous work with cerium catalyzed esterification of alkenes, cited in the background above, only looked at Ce(IV) sulfate as catalyst. Other Ce salts and supported Ce salts, however, show higher activity while maintaining high selectivity to the 2-isomer. The present inventors have discovered that high conversions and selectivity are obtained when the cerium catalyst has both Bronsted and Lewis acidity. Cerium (IV) catalysts are substantially more active than Ce(III) substrates. Thus, $Ce(SO_4)_2.4H_2O$ which possesses both Lewis acidity and Bronsted acidity from the complexation with waters of hydration is significantly more active than the anhydrous analog. $Ce(OSO_2CF_3)_4$ which is a stronger Lewis acid gives higher conversions than Ce(IV) sulfate at comparable conditions.

The Ce(IV) salt may also be dispersed on supports such as silica, MCM-41, and other per se well known catalyst support materials. There are numerous well known methods of dispersion of such salts such as insipient wetness impregnation.

The Ce(IV) silica supported catalysts can be prepared by dissolving the cerium(IV) catalyst, such as Ce(IV) sulfate in water, slowly adding in a support such as silica gel, mixing, removing the water, and drying the Ce(IV) supported catalyst. In one example, 3.53 grams of $Ce(SO_4)_2.4H_2O$ was dissolved in 60 mls of distilled water. To this solution, was added 3.33 grams of silica gel, and the resulting mixture stirred. The water was removed with a rotoevaporator, the catalyst collected and dried at 100° C. for 1 hour. The catalyst was used without further modification.

The dispersed Ce(IV) gives high conversions with high selectivity, as shown in the table above. It is possible that the Cerium may actually be incorporated into the framework of the support.

Other Lewis acid catalysts can give high conversions to the alkyl carboxylate but are not selective to the 2-isomer. Even other rare earth Lewis acid catalysts, such as Sc-triflate (shown in the table for comparison) and La-triflate, which give high conversions to the alkyl carboxylate, are not as selective for the 2-isomer. A range of carboxylic acids may be used, such as acetic acid, formic acid, propionic acid, and the like, are particularly desirable, with acetic acid preferred.

The α-methyl alkyl enriched carboxylate ester product of the first step may be hydrolyzed to convert the ester functionality to the corresponding secondary alcohol and allow recovery of the carboxylic acid. The hydrolysis of esters is well-known per se and may be carried out in a number of ways. One method involves ester cleavage under base conditions such as refluxing the carboxylate ester with alcoholic potassium hydroxide or aqueous sodium hydroxide. Other applicable methods to obtain the secondary alcohol would include chemical reduction with reagents such as lithium aluminum hydride or sodium borohydride or hydrogenation over one of a variety of nickel or palladium or platinum hydrogenation catalysts. These methods would not allow recovery of the carboxylic acid, however. One of skill in the art in possession of the present disclosure can perform the conversion to the desired product without undue experimentation.

The secondary alcohol from above may be reacted with phthalic anhydride or other acids to produce esters which are especially useful as PVC plasticizers. By way of example and without intending to be limiting, the phthalate ester of 2-octanol can be prepared by reacting 2.2 moles of 2-octanol with 1 mole of phthalic anhydride, using well known esterification conditions, under either a nitrogen atmosphere or an oxygen-free atmosphere obtained through vacuum or through a combination of nitrogen purging and applying a vacuum, using one of a variety of tin or titanium organometallic catalysts.

In a preferred embodiment, the secondary alcohol phthalate may be hydrogenated to yield the non-phthalate secondary alcohol cyclohexanoate diester. Suitable processes that can be used to hydrogenate these esters include catalytic hydrogenation of the aromatic esters over supported catalysts containing ruthenium, nickel, cobalt, copper, or rhodium, or combinations of these metals, in optionally fixed bed processes. These esters will be more effective as PVC plasticizers than esters derived from other secondary alcohols due to their high C2-OH content. Other plasticizing esters can be prepared by reacting these high C2-OH content alcohols with terephthalic acid, dimethyl terephthalate, trimellitic acid, citric acid, hexahydrophthalic anhydride or benzoic acid. The secondary alcohol may also be alkoxylated to produce highly desirable secondary alcohol surfactants.

The plasticizing esters can be used to form flexible PVC compositions. For example, these plasticizers can be mixed with suspension grade PVC resin, in a composition that can range from 20 to 100 parts of plasticizer per hundred parts of PVC resin (parts as used herein are parts by weight). The material is further heated under mixing, using techniques such as Banbury mixers, roll mills, calandars, extruders, or injection molding to produce flexible PVC compositions. The same plasticizers can be used to prepare plastisol compositions by mixing 40 to 100 parts of these plasticizers with 100 parts of a paste or emulsion grade PVC resin. Plastisols can be converted to flexible PVC articles upon heating from 160-200° C. Other additives can be added to these formulations included PVC stabilizers, fillers, secondary plasticizers, lubricants, colorants, pigments, and foaming agents. Applications for such flexible PVC compositions include wire and cable insulation or jacketing, vinyl flooring, PVC backed carpet, automotive underbody sealants, PVC adhesives, wall paper, synthetic leather, toys, shoes, traffic cones, coated fabrics, awnings, tarpaulins, films, tubing, and medical devices. In use with acrylic polymers, these plasticizers can be used to prepare acrylic caulks and sealants.

The invention has been described above with reference to numerous embodiments and examples, and many variations will suggest themselves to those skilled in this art. Preferred embodiments of the invention, however, may be described as follows: in a process for the preparation of secondary alcohols having the formula R—C(H)(OH)—CH$_3$, wherein R is an aliphatic hydrocarbon having from 1 to 18 carbon atoms, the process comprising contacting an alpha-olefin with a Ce(IV) catalyst having a higher acidity than Ce(IV) anhydrous sulfate in the presence of a carboxylic acid, in embodiments a carboxylic acid having from 1 to 8 carbon atoms (C1 to C8), preferably C1 to C3, more preferably C2 to C3, followed by hydrolysis to convert the ester functionality to the corresponding secondary alcohol, preferably wherein a mixture of alcohols is obtained, said mixture comprising at least 60% of said secondary alcohol, preferably from 70 to 100% secondary alcohol; and also one or more of the following preferred embodiments: wherein said Ce(IV) catalyst is selected from at least one of Ce(IV) salt dispersed on a support, Ce(SO$_4$)$_2$·4H$_2$O, and Ce(OSO$_2$CF$_3$)$_4$; wherein the catalyst includes a Ce(IV) salt dispersed on a support, said support selected from at least one of molecular sieves, silica, and alumina; wherein R is from 1 to 18 carbon atoms, such as from 1 to 14, or from 5 to 14, or from 6 to 10, or from 7 to 9 carbon atoms, or from any of the lower carbon numbers just given to any of the higher carbon numbers just given; wherein said carboxylic acid is selected from at least one of formic acid, acetic acid, propionic acid, butyric acid, isobutyric acid, pentanoic acid, isopentanoic acid, hexanoic acid, isoheptanoic acid, and 2-ethyl hexanoic acid, preferably formic, acetic, or propionic acids; wherein said hydrolysis includes reaction of the alkyl carboxylate ester with aqueous caustic solution or alcoholic KOH; or any of the aforementioned embodiments and further including a step of reacting said alcohol having the formula R—C(H)(OH)—CH$_3$ with an acid or anhydride selected from phthalic acid, cyclohexane dicarboxylic acid, hexahydrophthalic anhydride, terephthalic acid, dimethyl terephthalate, benzoic acid, citric acid, trimellitic anhydride or benzoic acid (or mixtures of these acids or anhydrides) to yield the corresponding ester. Another preferred embodiment is a composition comprising an ester of a mixture of secondary alcohol made by the process of the invention, said alcohol having the hydroxyl group predominantly at the C2 position, such as in the ranges set forth herein (i.e., at least 60%, such as from 60% to nearly 100%) and a plasticizable resin, such as wherein said plasticizable resin is PVC. Yet another preferred embodiment of the invention includes the step of converting said secondary alcohol mixture obtained by the process of the invention to a surface active agent, wherein said secondary alcohol mixture is converted to a nonionic detergent by reaction with ethylene oxide or propylene oxide or mixtures of ethylene and propylene oxide, or the step of converting the secondary alcohol mixture obtained by the process of the invention to a surface active agent, wherein said secondary alcohol mixture is sulfated, or the step of converting said secondary alcohol mixture obtained by the process of the invention to a surface active agent, wherein said secondary alcohol mixture is polyethoxylated, then sulfated, and then neutralized with sodium hydroxide or ammonium hydroxide, or the step of converting said secondary alcohol mixture to a surface active agent, wherein said secondary alcohol mixture is halogenated and condensed with a tertiary amine to form a cationic quaternary nitrogen surfactant, or the step of converting said secondary alcohol mixture to a surface active agent, wherein said secondary alcohol mixture is reacted with phosphorus pentaoxide to produce a phosphate ester surfactant. Preferred embodiments of the invention also include the use of the secondary alcohol mixture so treated by conversion of one of the additional steps mentioned above (e.g., reaction with ethylene oxide or propylene oxide, etc.) in detergents, cleaning solutions, personal care products, and for enhanced oil recovery.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

What is claimed is:

1. A process for the preparation of secondary alcohols having the formula R—C(H)(OH)—CH$_3$, wherein R is an aliphatic hydrocarbon having from 1 to 18 carbon atoms, the process comprising contacting an alpha-olefin with Ce(OSO$_2$CF$_3$)$_4$ in the presence of a carboxylic acid, followed by hydrolysis to convert the ester functionality to the corresponding secondary alcohol, wherein a mixture of alcohols is obtained, said mixture comprising at least 60 mol % of said secondary alcohol, based on the total amount of alcohol in said mixture.

2. The process of claim 1, wherein Ce(OSO$_2$CF$_3$)$_4$ is disposed on a support and said support selected from at least one of molecular sieves, silica, and alumina.

3. The process of claim 1, wherein R is from 4 to 10 carbon atoms.

4. The process of claim 1, wherein said mixture of alcohols has from 80 mol % to 99 mol % of said secondary alcohols, based on the total amount of alcohol in said mixture.

5. The process of claim 1, wherein said hydrolysis includes reaction of the alkyl carboxylate ester with aqueous caustic solution or alcoholic KOH.

6. The process of claim 1, characterized by a conversion of said olefin to alcohol of at least 40 mol %, when conducted at conditions of 85-95° C. and atmospheric pressure.

* * * * *